United States Patent
Hubel et al.

(10) Patent No.: US 9,556,412 B2
(45) Date of Patent: Jan. 31, 2017

(54) INLET AND OUTLET GEOMETRIES FOR A VERTICAL THREE-STREAM MICROFLUIDIC DEVICE

(71) Applicant: Regents of the University of Minnesota, Minneapolis, MN (US)

(72) Inventors: Allison Hubel, St. Paul, MN (US); Jacob Hanna, Watertown, WI (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/394,693

(22) PCT Filed: Apr. 17, 2013

(86) PCT No.: PCT/US2013/036933
§ 371 (c)(1),
(2) Date: Oct. 15, 2014

(87) PCT Pub. No.: WO2013/158737
PCT Pub. Date: Oct. 24, 2013

(65) Prior Publication Data
US 2015/0111241 A1    Apr. 23, 2015

Related U.S. Application Data

(60) Provisional application No. 61/625,498, filed on Apr. 17, 2012.

(51) Int. Cl.
*C12M 1/00* (2006.01)
*B01L 3/00* (2006.01)

(52) U.S. Cl.
CPC ........... *C12M 47/12* (2013.01); *B01L 3/50273* (2013.01); *B01L 3/502753* (2013.01);
(Continued)

(58) Field of Classification Search
CPC .... C12M 47/12; C12M 47/02; B01L 3/50273; B01L 3/502753; B01L 2400/0409; B01L 3/502776; B01L 2300/0861; B01L 3/502761
See application file for complete search history.

(56) References Cited

U.S. PATENT DOCUMENTS

| 3,713,778 A | 1/1973 | Karamian |
| 4,798,579 A * | 1/1989 | Penhasi ................. B04B 5/0442 494/16 |

(Continued)

FOREIGN PATENT DOCUMENTS

| GB | 1046291 A | 10/1966 |
| WO | WO-2013158737 A1 | 10/2013 |

OTHER PUBLICATIONS

Fleming, K. K., et al., "Numerical Characterization of Diffusion-Based Extraction in Cell-Laden Flow Through a Microfluidic Channel", *Journal of Biomedical Engineering*, 129, (2007), 703-711.

(Continued)

*Primary Examiner* — David C Mellon
(74) *Attorney, Agent, or Firm* — Schwegman Lundberg & Woessner, P.A.

(57) ABSTRACT

An example includes an apparatus for separating cells from a fluid sample, including a plenum, defining: a centrally located top inlet, and respective side outlets disposed below the inlet and to the side of the inlet; and a bottom outlet disposed below the top inlet, to the side of the two or more outlets, wherein the plenum is configured to receive a fluid and cells suspension through the inlet, and direct it to the bottom outlet, against respective side-walls extending between the bottom outlet and the two or more side outlets, and wherein the distance between each of the two or more side outlets and the bottom outlet is selected to encourage (Continued)

cells to exit through the bottom outlet under a force. Lateral/vertical distance between the inlet and side outlets can provide lateral fluid travel, thereby allowing time for gravity to bias cells toward an outlet.

24 Claims, 11 Drawing Sheets

(52) U.S. Cl.
CPC ........ *C12M 47/02* (2013.01); *B01L 3/502761* (2013.01); *B01L 3/502776* (2013.01); *B01L 2300/0861* (2013.01); *B01L 2400/0409* (2013.01)

(56) References Cited

U.S. PATENT DOCUMENTS

| | | | |
|---|---|---|---|
| 5,932,100 A | 8/1999 | Yager et al. | |
| 6,432,630 B1* | 8/2002 | Blankenstein | B01D 57/02 |
| | | | 422/186 |
| 9,033,858 B2* | 5/2015 | Katz | B04B 11/00 |
| | | | 494/45 |
| 2004/0072278 A1* | 4/2004 | Chou | B01L 3/502761 |
| | | | 435/29 |
| 2005/0037333 A1 | 2/2005 | Pham | |
| 2006/0169589 A1* | 8/2006 | Takagi | G01N 27/44752 |
| | | | 204/515 |
| 2007/0119754 A1* | 5/2007 | Takagi | B03C 7/12 |
| | | | 209/127.1 |
| 2009/0236269 A1* | 9/2009 | Kojima | B03B 5/00 |
| | | | 209/655 |
| 2014/0193381 A1* | 7/2014 | Warner | A61M 5/1407 |
| | | | 424/93.7 |
| 2016/0045921 A1* | 2/2016 | Taga | B01D 21/262 |
| | | | 494/37 |

OTHER PUBLICATIONS

Mata, C., et al., "Experimental study of diffusion-based extraction from a cell suspension", *Microfluid Nanofluid*, 5(4), (2008), 529-540.

"International Application Serial No. PCT/US2013/036933, International Search Report mailed Jul. 10, 2013", 3 pgs.

"International Application Serial No. PCT/US2013/036933, Written Opinion mailed Jul. 10, 2013", 5 pgs.

Glass, K. K. Fleming, "Optimization of a microfluidic device for diffusion-based extraction of DMSO from a cell suspension", International Journal of Heat and Mass Transfer, 51, (2008), 5749-5757.

"European Application Serial No. 13718763.9, Office Action mailed Nov. 26, 2014", 2 pgs.

"European Application Serial No. 13718763.9, Response filed Jun. 1, 2015 to Office Action mailed Nov. 26, 2014", 13 pgs.

"International Application Serial No. PCT/US2013/036933, International Preliminary Report on Patentability mailed Oct. 30, 2014", 7 pgs.

* cited by examiner

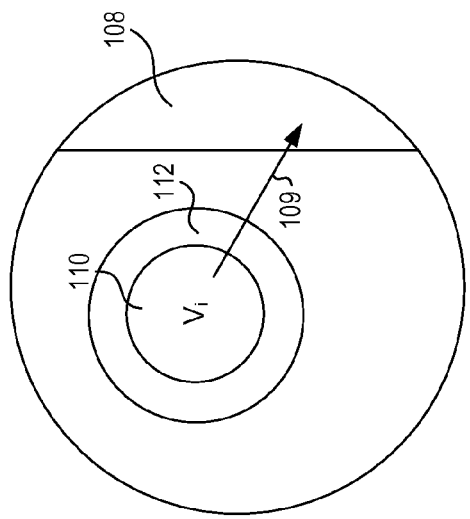
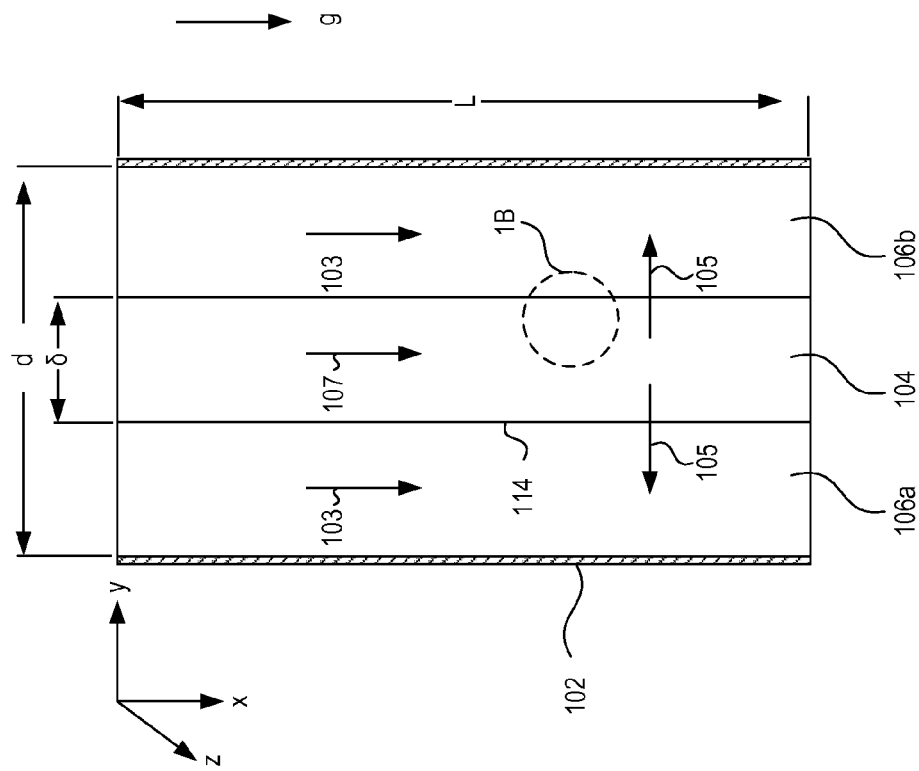
FIG. 1B
FIG. 1A 406  408

INLET AND OUTLET GEOMETRIES FOR A VERTICAL THREE-STREAM MICROFLUIDIC DEVICE

CLAIM OF PRIORITY

This patent application is a U.S. National Stage Application filed under 35 U.S.C. §371 from International Application Serial No. PCT/US2013/036933, which was filed Apr. 17, 2013, and published as WO 2013/158737 on Oct. 24, 2013, and which claims the benefit of priority of U.S. Provisional Patent Application Ser. No. 61/625,498, entitled "INLET AND OUTLET GEOMETRIES FOR A VERTICAL THREE-STEAM MICROFLUIDIC DEVICE," to Allison Hubel et al., filed on Apr. 17, 2012, which applications are hereby incorporated by reference as if reproduced herein and made a part hereof in their entirety, and the benefit of priority of each of which is claimed herein.

BACKGROUND

Cells can be treated with chemicals or other agents to obtain certain benefits. For example, cells are routinely cryopreserved for investigative and therapeutic applications. However, a common cryoprotective agent (CPA), dimethyl sulfoxide (DMSO), which is used to protect cells from the stresses of freezing and thawing, can be toxic, and agents such as DMSO should be removed before cells are used in certain processes.

SUMMARY

The present inventors have recognized, among other things, that a problem to be solved can include removing agents from a fluid sample. The present subject matter can help provide a solution to this problem, such as by providing a microfluidic device in which three streams flow, such as vertically, such as in parallel, through a rectangular channel. Two wash streams can flow on either side of a stream, such as a DMSO-laden cell stream, allowing an agent such as DMSO to diffuse into the wash and be removed. The washed sample can be collected.

The present inventors have recognized, among other things, that a problem to be solved can include recovering a high percentage of cells while an agent is removed from a flowing sample. The present subject matter can help provide a solution to this problem, such as by providing extraction of DMSO from a cell stream at flow rates of from around 0.5 to around 4.0 ml/min (Pe=1263-10,100). Both higher and lower cell stream flow rates can be achieved by scaling of the channel and plenum. Cells from which agents are recovered can include lymphoblasts (e.g., Jurkat cells) in suspensions, such as suspensions ranging from 0.5% to 20% cells by volume. Cell recovery can be greater than 95%. Agent removal, such as DMSO removal, can be done along the device's length. Embodiments provide a high cell recovery that can be around 25% better than established cell washing techniques. Embodiments can provide high flow rates, allowing for processing of clinically relevant cell populations.

Certain embodiments provide for processing without expensive or heavy equipment, enabling a wide range of field-uses. Embodiments can be used for processing of cells for cell therapy and regenerative medicine, cell banking, and processing of biospecimens, among other uses.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 1A shows a schematic of a flow configuration within the channel, according to an embodiment.

FIG. 1B is a close up of the section 1B in FIG. 1A.

DETAILED DESCRIPTION

Figure 2:
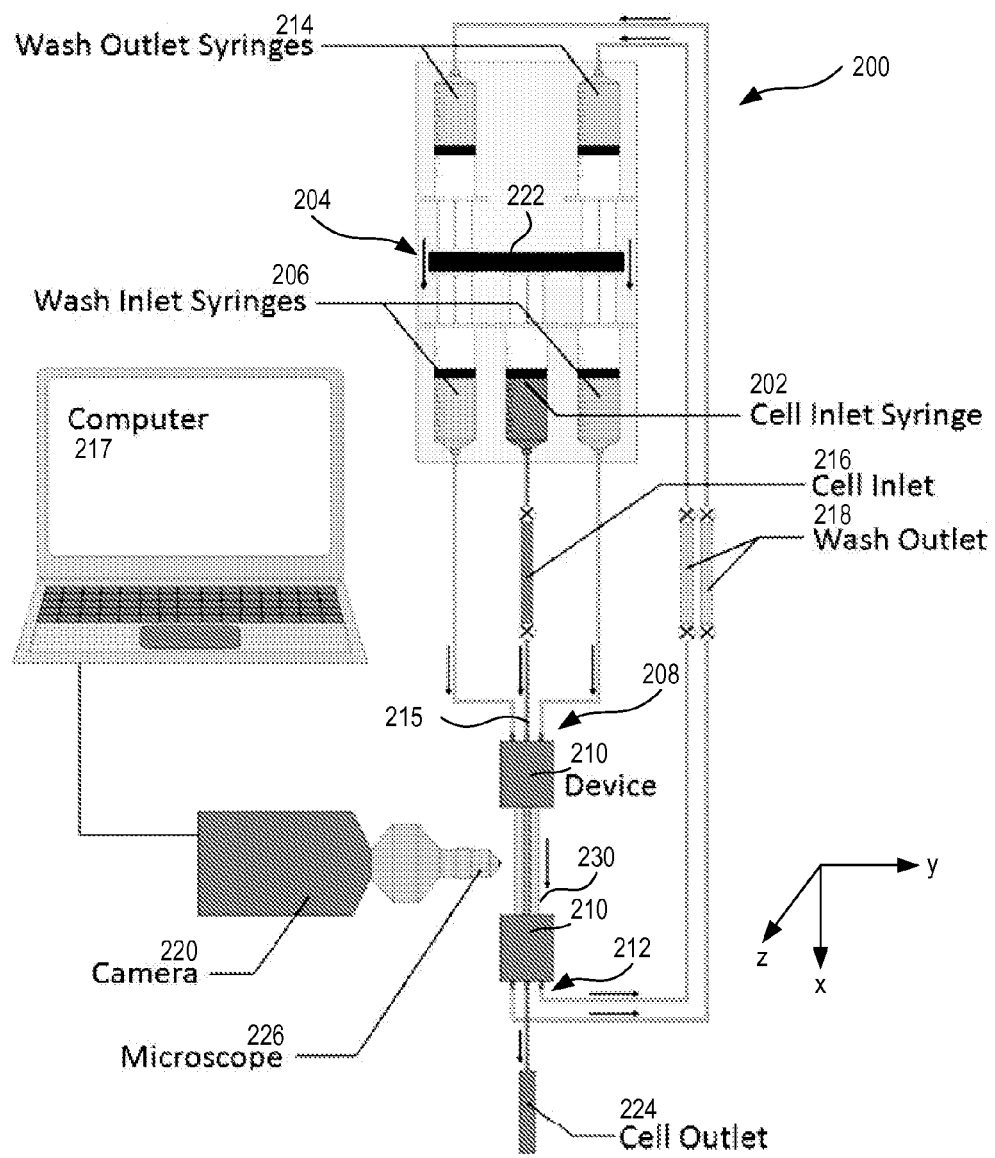
FIG. 2 shows a schematic of an example setup including a device, a syringe pump, connections, observational equipment, and sample collection points.

Cryopreservation is an enabling technology for a wide variety of fields including cellular therapy/regenerative medicine, biobanking, and production of recombinant proteins. Cells that are cryopreserved can require the introduction of cryoprotective agents ("CPA") to provide protection for the cell from the stresses of the freeze-thaw process. One cryoprotective agent, dimethylsulfoxide ("DMSO"), can be used at concentrations such that introduction or removal of the solutions can result in cell lysis.

DMSO can be toxic to cells and can cause negative side effects when infused into patients receiving cell-based therapies. DMSO can be removed from cell samples by repeated centrifugation and replacement of the supernatant with a wash solution. However, a sample can incur cell losses of 27-30% due to centrifugation and osmotic forces. Automated cell washers can reduce labor requirements, but still can result in similar cell losses.

Microfluidic devices can manipulate cell populations. These devices can provide for cell counting, sorting of heterogeneous cell populations, and controlling exposure to reagents, among other benefits. Examples can separate cells based on size, fluorescence labeling and deflecting with electromagnetic (EM) fields, magnetic forces, acoustic fields, and differential cell settling due to gravity, among other approaches. Microfluidic devices can be used for performing dose-dependent cell assays, as well as exchanging cell carrier medium. An ability to manipulate cells and the chemical environment surrounding them can make microfluidic devices useful for cryopreservation applications.

Extraction of CPAs in microfluidic devices can be dominated by diffusion, which can result in gradual shifts in concentration. This effect can reduce osmotic stresses on cells when compared to step changes produced by some conventional centrifuge-based washing techniques. Cell motion can be gentle due to the laminar nature of flow. Some contemporary examples use microfluidic devices for introduction and removal of CPA from cell samples, which can improve cell viability compared to standard protocols, but flow rates can be limited to 20 µl/min. Some contemporary microfluidic devices can handle cell suspensions only at very low cell concentrations.

In practice, many cryopreservation applications use cell volume fractions ("CVF") of 2-20%, and devices that achieve flow rates of around 1-2 ml/min are desirable. A contemporary example includes a multi-stage microfluidic device capable of achieving 95% removal of DMSO under these conditions. Each stage of the device consists of a horizontally-oriented, rectangular cross-section channel. Two streams can flow through the channel in parallel and in contact; a cell- and DMSO-laden sample stream can flow along the bottom, while a phosphate-buffered saline ("PBS") wash solution can flow along the top. DMSO diffuses from the sample stream to the wash stream, and the two streams can be separated at the outlet, thereby removing DMSO from the sample. However, cell recovery from the device may be high only under a specific range of flow conditions, restricting the operating window for DMSO removal. The location of cells near the channel bottom also exposes them to significant shear gradients due to the parabolic flow profile, thereby increasing cell loss. Additionally, the device exhibits a significant startup time where cell recovery can be low due to cells settling into the low velocity flow near the channel bottom.

To address these concerns, and provide other benefits, embodiments of the present subject matter provide an improved system and method that mitigates cell recovery issues referenced above while improving DMSO removal. Certain embodiments use three streams flowing downward in parallel through a device. Wash streams can be located on one or more sides of a sample stream (e.g., cells and DMSO). Wash streams can be located on opposite sides of a middle sample stream. Diffusion-based extraction of CPAs can result from the microfluidic environment (e.g., short cross-stream distances and laminar flow) established within the channel. Compared to contemporary designs, embodiments can increase the interfacial area between streams and shorten diffusion distances, reducing the downstream distance required for removal of DMSO from the sample stream. Cell motion in certain embodiments can be controlled by placing a stream including cells in the center, e.g. the region of lowest shear in the microfluidic device, which can reduce stresses on the cells. This orientation can leverage an external force such as gravity to improve cell recovery from the device.

A schematic of a three-stream, vertical microchannel is shown in FIGS. 1A and 1B. The schematic shows a flow configuration within the microchannel 102. A cell stream 104, which can include a CPA-laden cell suspension, can flow 107 vertically downward through the center of the channel. A CPA-free wash solution, e.g. 106a and/or 106b, can flow 103 in parallel downward on one or both sides of the cell stream. CPA can diffuse 105 from the cell stream 104 to one or more adjacent wash streams 106a, 106b. The length L can be selected to provide for a desired amount of diffusion. The sectional view of FIG. 1B depicts transport 109 of CPA across the cell membrane 112 from the intracellular space 110 to the extracellular space 108.

The microchannel 102 can include a rectangular cross-section channel 114, which can be 500 µm deep (y-direction), 25 mm wide (z-direction) and 80 mm long (x-direction), through which three streams can flow. A center stream 104 can contain a DMSO solution that may or may not contain cells, whereas two side streams 160a, 106b can contain a wash solution. All three streams can flow in the x-direction (e.g., vertically downward) in parallel and in contact with one another within the channel.

Flow within the channel can be laminar due to the small cross-stream dimension and a low Reynold's number (Re from about 2 to about 12). Transport of CPA from the cell-laden stream to the wash streams can be attributed, in some cases solely, to cross-stream diffusion (y-direction), driven by the concentration gradient from the high-concentration cell-laden stream to the lower-concentration wash streams. Cells can remain concentrated in the central stream due to their long characteristic diffusion time as compared to a typical CPA molecule as well as the low shear gradients in the channel center.

The design of the microchannel 102 geometry and selection of operating conditions for a device including the microchannel 102 can be based upon a theoretical model of device behavior. A diffusion behavior of CPA within the microfluidic channel can be predicted using a modification of the convection-diffusion equation, with one or more of the following four assumptions: (1) flow within the channel can be laminar, steady-state, and two-dimensional. The entrance length of the channel can be assumed to be negligibly short. Thus the velocity in the channel can be in the x-direction and can be a function of y only. (2) Cells can be homogeneously distributed throughout the cell stream fluid, can be neutrally buoyant, and can move with the local fluid velocity. (3) Diffusion of CPA from the intracellular to the extracellular space can be modeled as a uniform "source" term for the local fluid as cells can be small and disperse. (4) Based on scaling analysis, diffusion can be the dominant mode of CPA transport in the cross-stream (y) direction, and convection can dominate in the downstream (x) direction. Diffusion can be negligible in the x and z directions, and there can be little or no convection in the y or z directions. Some or all of these assumptions can yield the following convection-diffusion equation:

$$v_x \frac{\partial c_t}{\partial x} = \frac{D}{dU}\left(\frac{\partial c_t}{\partial y^2}\right) + \frac{Bd}{U}\left(\frac{V_i}{V_t}\right)(c_i - c_e) \quad (1)$$

where $v_x$ is the local fluid velocity in the x-direction, D is the diffusivity of the CPA, d is the channel depth (y-direction), U is the average fluid velocity in the channel, $c_t$ is the local extracellular CPA concentration, B is the modeling permeability of the cell membrane to the CPA (membrane permeability divided by membrane thickness), $V_i$ is the intracellular volume, $V_t$ is the local volume (intracellular and extracellular), and $c_i$ and $c_e$ denote the local CPA concentrations in the intracellular and extracellular spaces, respectively. The first term references convection of CPA downstream in the channel. The second term references the cross-stream diffusion behavior. The third term acts as a source of CPA in the local fluid, and references the transport of CPA across the cell membrane to the extracellular space.

From Eq. 1, three dimensionless parameters become apparent:

$$Pe = \frac{dU}{D} \quad (2)$$

$$B^* = \frac{Bd}{U} \quad (3)$$

$$\frac{V_i}{V_t} \quad (4)$$

Pe is the Péclet number, which references the relative importance of convective to diffusive transport of CPA. B* compares the rate at which CPA is transported from the intracellular space to downstream convection. $V_i/V_t$ represents the portion of the local volume occupied by cells, and hence how much CPA should be transported to the extracellular space before diffusing to the wash streams. Since it is assumed that there are few or no cells in the wash streams, $V_i$ can equal or be close to zero in the wash streams, and the influence of the third term of Eq. 1 can be reduced or dropped.

An additional parameter of interest can be the depth fraction, $$\delta/d \frac{\delta}{d},$$

or the portion of the channel depth that can be occupied by the cell stream. This can be related to the volumetric flow rate fraction through the parabolic velocity profile within the channel. The flow rate fraction can be defined by equation (5) where $q_c$ represents the volumetric flow rate of the cell stream 104, $q_t$ is the total volumetric flow rate through the microchannel 102 (e.g., a combination of cell stream 104 and wash streams 106a, 106b), and $q_w$ can represent volumetric flow rate of the wash streams in total, with 106a representing 0.5 $q_w$ and 106b representing 0.5 $q_w$. The flow rate fraction can affect the diffusion behavior in the channel by altering the relative volumes of CPA-laden (cell) and CPA-free (wash) streams, as well as the average distance a CPA molecule must diffuse to exit the cell stream.

A Reynolds number, defined by (6), where ρ is the fluid density and μ is the viscosity of the fluid, can be of importance for its indication of flow stability within the channel.

$$f_q = \frac{q_c}{q_t} \quad (5)$$

$$Re = \frac{\rho U d}{\mu} \quad (6)$$

Eq. 1 can be solved numerically using a forward-marching finite difference calculation. The solution domain can be initialized by setting the entire cell stream to the inlet concentration of CPA and cell volume fraction. Both wash streams can be set to zero CPA concentration. No-flux and no-slip boundary conditions can be applied at the channel walls. A developed parabolic velocity profile can be applied throughout the entire domain. The resulting computational model can be solved using MATLAB.

FIG. 2 provides a schematic of a setup 200, including devices 210, a syringe pump 204, connections, observational equipment, and collection points. A microchannel 230 (e.g., 102 in FIG. 1) can be disposed between the devices 210 as illustrated. Although two devices 210 are illustrated, examples contemplated include a device 210 at the inlet 208 only and a device 210 at the outlet 212 only.

According to some embodiments, a cell inlet syringe 202 containing the cell suspension (e.g., cells with DMSO in solution) can be driven by a syringe pump 204. One or more wash inlet syringes 206 containing wash solutions (e.g., PBS) can be driven by the same syringe pump 204 or another pump, and connected to the device inlet 208 via tubing such as 3/16" inner diameter ("ID") silicone tubing. The three streams can be flowed in parallel contact through the device 210, before being separated at the device outlet 212. In addition to any pressure applied by the syringe pump 204, flow through the devices 210 can be influenced by an external force such as gravity. Wash stream flow rates can be controlled by a set of wash outlet syringes 214 that can be drawn by the same syringe pump 204 or another pump. Flow can be driven by various types of pumps (e.g. peristaltic, syringe) and/or by gravity.

A cell outlet 224 and wash outlets 218 can comprise one or more segments of removable tubing that can be used to collect samples. The cell outlet 224 can precede the inlet 208, and wash outlets 218 can be coupled to the outlet 212. The cell outlet 224 can include cells from the cell stream 215 originated from the cell inlet syringe 202 and can be open to the atmosphere. Cells from the cell outlet 224 can be collected, such as in a vial. Additionally, a microscope 226 and camera 220 can be set up to observe cell motion within the microchannel 230.

Volumetric flow rates through the three streams can be controlled via a syringe pump 204, such as a Harvard Apparatus, Inc. Model 22 pump. The flow rate for the cell-laden stream can be set via the pump controller, such that a piston 222 drives the syringe at the desired flow rate (e.g., within a tolerance of +/−0.1 ml/min) The same piston can be used to drive the two wash stream inlet syringes. Because the piston 222 can move all three inputs at the same velocity, the relative volumetric flow rates of the cell stream compared to the wash streams can be determined by the relative cross-sectional areas of the syringes. Each of the wash inlet syringes 206 can be paired with a similar or identically sized wash outlet syringe 214 mounted on the reverse side of the piston 222 such that these wash outlet syringes 214 draw an equal volume of wash from the outlet 212 as enters the device at the device inlet 208.

The initial concentration used in the studies can be 10% DMSO by volume, and the concentration used in several cryopreservation protocols such as those for hematopoietic stem cell products. DMSO concentration in the cell and wash outlet streams can be determined by spectrophotometry using methods described herein. For example, concentration can be correlated to the sample's absorbance of light at a wavelength of 209 nm, and can be measured using a SpectraMax™ Plus 384 spectrophotometer manufactured by Molecular Devices, Inc. To correlate sample absorbance to a known concentration, a calibration curve can be created by serially diluting a sample of stock solution (10% DMSO by volume) over a range of normalized concentrations from C*=1.0 to 0.0001 (10% to 0.001% DMSO). Calibration measurements can be performed in triplicate for accuracy. The relation between absorbance and concentration can be non-linear. However, it may be approximated as linear for absorbencies ranging from approximately 0.6 to 1.2 optical density (OD). This region can have a high sensitivity (for example, demonstrating a large change in OD for small changes in concentration).

Samples can be taken from the cell stream outlet, as well as both wash outlet streams, for measurement of DMSO concentration. In embodiments using cells, the samples can be centrifuged to remove cells prior to spectrophotometry Similar to the calibration curve, samples can be serially diluted, such as in triplicate. Absorbency measurements falling within the linear region of the calibration curve can be selected and the actual concentration of the samples can be calculated using a fit expression for the linear region as well as the known number of dilutions of the sample.

Cell behavior within the device can be investigated using an immortalized lymphoblast cell line such as Jurkat cells as a model cell. Device performance can be quantified by tracking cell recovery defined as $$\text{Recovery} = \frac{\text{viability}_{out}}{\text{viability}_{in}} \times \frac{CVF_{out}}{CVF_{in}} \quad (7)$$

where viability can be the portion of living cells versus total cells in a sample, and cell volume fraction ("CVF") represents the fraction of the sample volume occupied by cells, or a measure of how many cells can be disposed in a sample. This measure can quantify one or both of cell losses resulting from cells damaged within the device as well as cells lost to the wash stream or retained in the device. Cell volume fraction can be determined using a hemocytometer, such as one manufactured by Hausser Scientific. A sample size, such as one having a minimum of 200 cells, can be counted for each cell stream sample. Viability can be determined using a membrane integrity dye, which in some embodiments can include a mixture of propidium iodide and acridine orange.

As shown in FIG. 2, samples can be collected immediately preceding the cell outlet 224 to the device, at the cell outlet 224, and at the wash outlets 218. Samples can be taken from the cell outlet 224 and can be used as a reference. Recovery at the cell outlet 224 can provide a measure of one or both of the devices 210. Samples taken from the wash outlets 218 can be used to determine if cells are being lost to the wash streams, or remain within the device itself. Also, because the cells are slightly denser than the surrounding fluid, cells can settle over time. For this reason, samples can be taken from the device within 10 minutes of cell suspension preparation, such as to ensure a homogeneous distribution of cells entering and exiting the device. The cell inlet 216 and outlet 224 can be separated by less than around 1 mL of fluid (depending on $f_q$) so time-dependent discrepancies in cell concentration should can be reduced or minimized.

In addition to tracking cell recovery at various sample locations, cell motion within the device can be qualitatively observed using a camera 220 attached to a microscope 226. A microscope 226 can be used to observe nearly the entire operational segment of the device, from two perpendicular angles (e.g., along the y and z directions). Image data can be stored and processed by a computer 217.

Processes can be performed to demonstrate a device's ability to remove DMSO from a stream that does not contain cells. DMSO ("cell") stream flow rates can be varied from 0.45 to 4.0 ml/min for three flow rate fractions, $f_q$=0.15, 0.19 and 0.33. A similar set of processes can be also performed for a single flow rate fraction using a two-stream, horizontally oriented device, for comparison with an example of the present subject matter. These and other embodiments can determine the DMSO concentration at the device outlet.

Figure 3A:
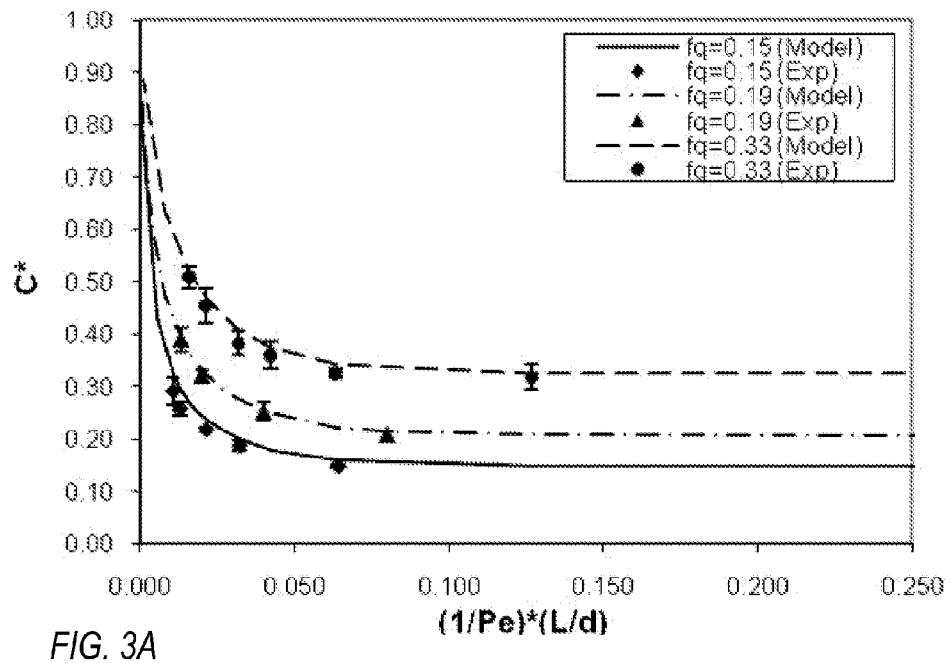
FIG. 3A shows plot representing DMSO removal in a device without cells present, according to an embodiment.
Figure 3B:
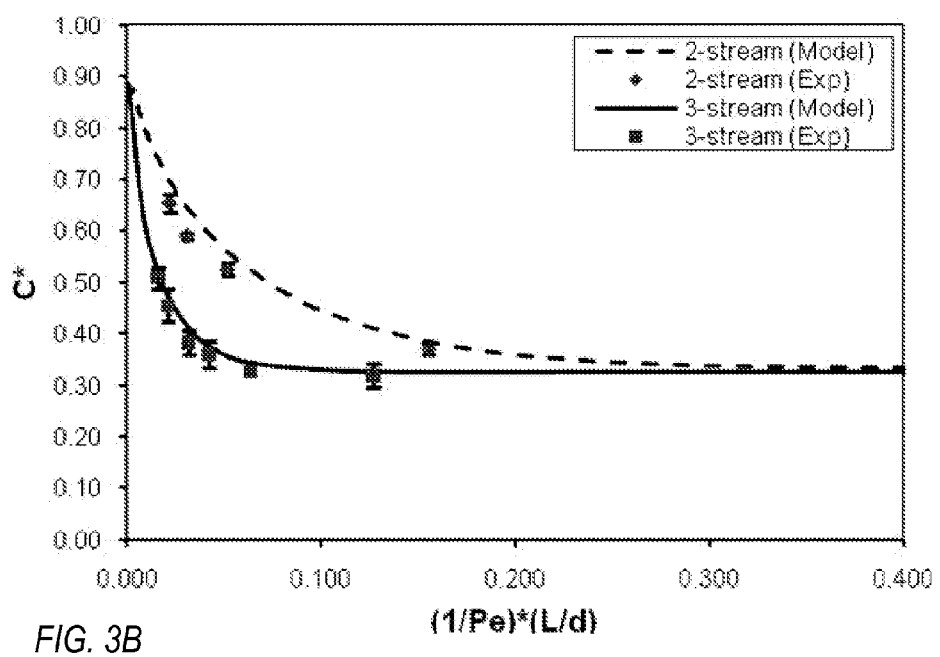
FIG. 3B shows a plot representing a comparison of DMSO removal in a three-stream, vertical device to a two-stream, horizontal device, according to an embodiment.

FIGS. 3A-3B show a normalized DMSO concentration, defined as $C^*=C_c/C_o$, where $C_c$ is the "cell" stream concentration and $C_o$ is the original sample concentration, versus the dimensionless parameter (1/Pe)*(L/d). FIG. 3A shows a plot of C* vs (1/Pe)*(L/d) showing DMSO removal of the device without cells present. Each of the three series represents embodiments at a different flow rate fraction (fq). Curves are also plotted showing the numerical model predictions for DMSO extraction. Each point represents the average of at least three separate experiments, and error bars denote one standard deviation. FIG. 3B shows a plot of C* vs (1/Pe)*(L/d) comparing DMSO removal in the three-stream, vertical device to the two-stream, horizontal device for $f_q$=0.33. Again, lines represent modeled approaches and each point shows the average of at least three separate experiments.

Extraction behavior of devices of varying aspect ratios can collapse to a single curve when plotted versus (1/Pe)*(L/d), which can be useful in scaled-up applications of the device. Also, each data point represents the average of a minimum of three separate experiments, with error bars showing one standard deviation. The plotted lines show the outlet concentration predicted by the numerical model, for comparison with certain experimentally determined values.

Table 1 shows the influence of cell population density on the DMSO-removal characteristics for several embodiments. The table shows effects of CVF on DMSO concentration at cell stream outlet for fq=0.33. Results represent DMSO removal with cells. Processes can be performed with CVF=0.5% and 15%, as well as acellular embodiments. Results show normalized DMSO concentration at the cell stream outlet, as average±one standard deviation. Three or more iterations can be performed at each condition for acellular and CVF=0.5%, and a single trial at each condition for CVF=15%, although the present subject matter is not limited to these numbers of iterations.

DMSO can penetrate the cell membrane and therefore can first leave the cells and then diffuse into the wash stream.

TABLE 1

| CVF | Pe | (1/Pe)*(L/d) | C* (exp) | C* (model) |
|---|---|---|---|---|
| 0 | 1263 | 0.127 | 0.43 ± 0.07 | 0.33 |
|  | 3788 | 0.042 | 0.40 ± 0.04 | 0.38 |
|  | 6313 | 0.025 | 0.45 ± 0.03 | 0.44 |
|  | 8838 | 0.018 | 0.50 ± 0.03 | 0.50 |
| 0.5% | 1263 | 0.127 | 0.47 ± 0.09 | 0.34 |
|  | 3788 | 0.042 | 0.41 ± 0.04 | 0.39 |
|  | 6313 | 0.025 | 0.45 ± 0.03 | 0.46 |
|  | 8838 | 0.018 | 0.51 ± 0.02 | 0.51 |
| 15% | 1263 | 0.127 | 0.50 | 0.37 |
|  | 3788 | 0.042 | 0.48 | 0.43 |
|  | 6313 | 0.025 | 0.49 | 0.50 |
|  | 8838 | 0.018 | 0.55 | 0.56 |

Embodiments can be performed with Jurkat cells as a model for hematopoietic stem cells for a CVF of 0.5% and 15%. The cells can be suspended in a 10% vol/vol DMSO solution. As with other experiments disclosed herein, the wash stream can include PBS. Processes can be performed with $f_q$=0.33 and cell stream flow rates from $Q_c$=0.5 to 3.5 ml/min. In Table 1, C* (exp) shows the normalized DMSO concentration at the cell stream outlet as the average±one standard deviation. C* (model) is the DMSO concentration that can be predicted by a numerical model, such as for comparison.

Figure 4A:
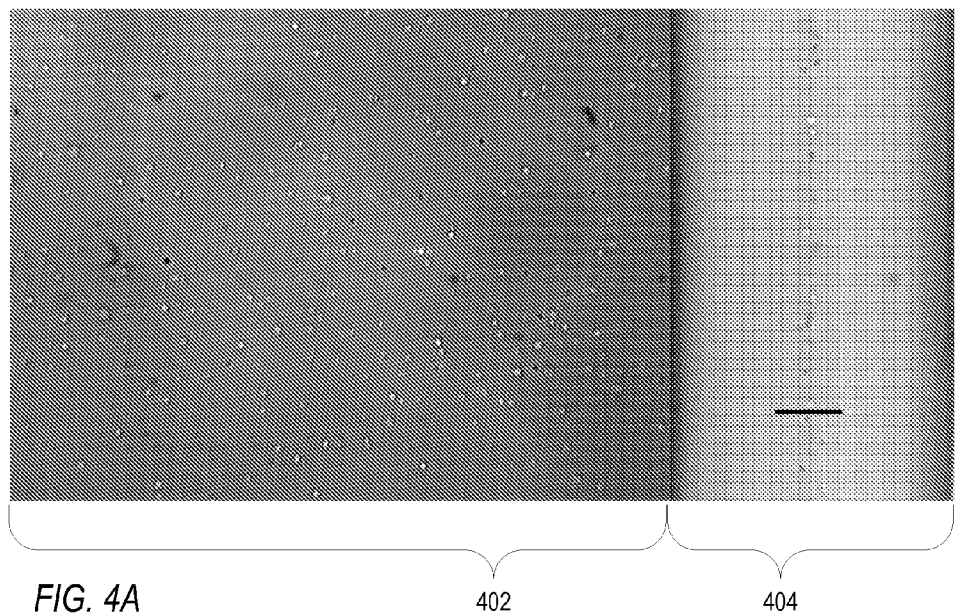
FIG. 4A shows images of cells within the device near an inlet, according to an embodiment.
Figure 4B:
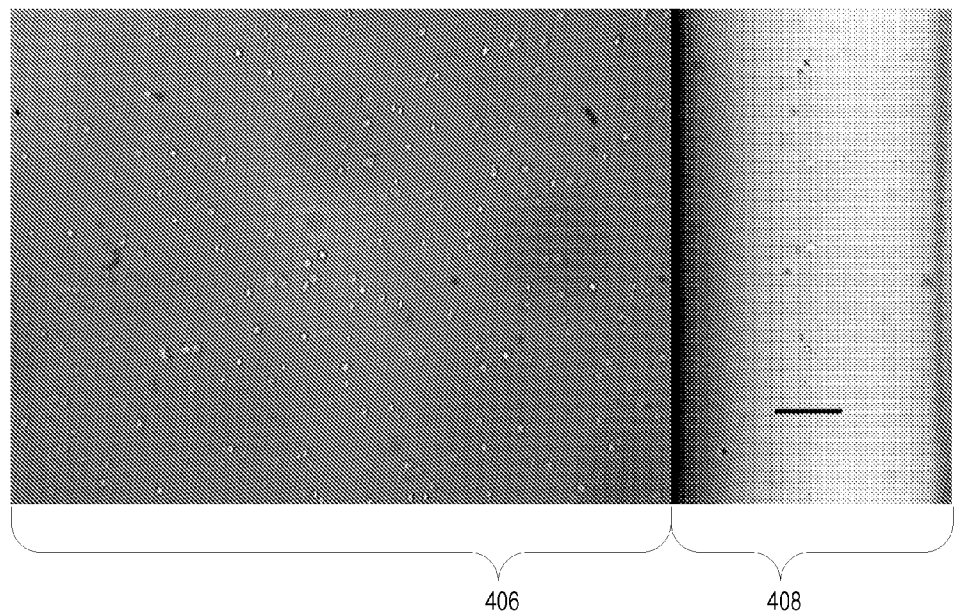
FIG. 4B shows images of cells within the device near an outlet, according to an embodiment.

Images of cell motion can be taken from a microscope using 10× magnification and Brightfield illumination. FIGS. 4A-B show Brightfield microscope images of cells within the device (10× magnification). In FIG. 4A, image 402 shows an en face view (the x-z plane as specified in FIG. 1) near the channel inlet, and image 404 shows a cross-sectional view (the y-x plane as specified in FIG. 1) view near the inlet showing the cell stream flowing between two wash streams. The scale bar denotes 115 μm. In FIG. 4B, image 406 shows an en face view near the outlet, and image 408 shows a cross-sectional view near the outlet. Processes can be performed using $f_q$=0.33 and cell stream flow rates between 0.5 and 1.5 ml/min (Pe=1263-3788), with CVF=0.5%. Images can be taken at several locations across the face view (i.e., the y-direction) to assess the uniformity of cell distribution throughout the cell stream.

Figure 5A:
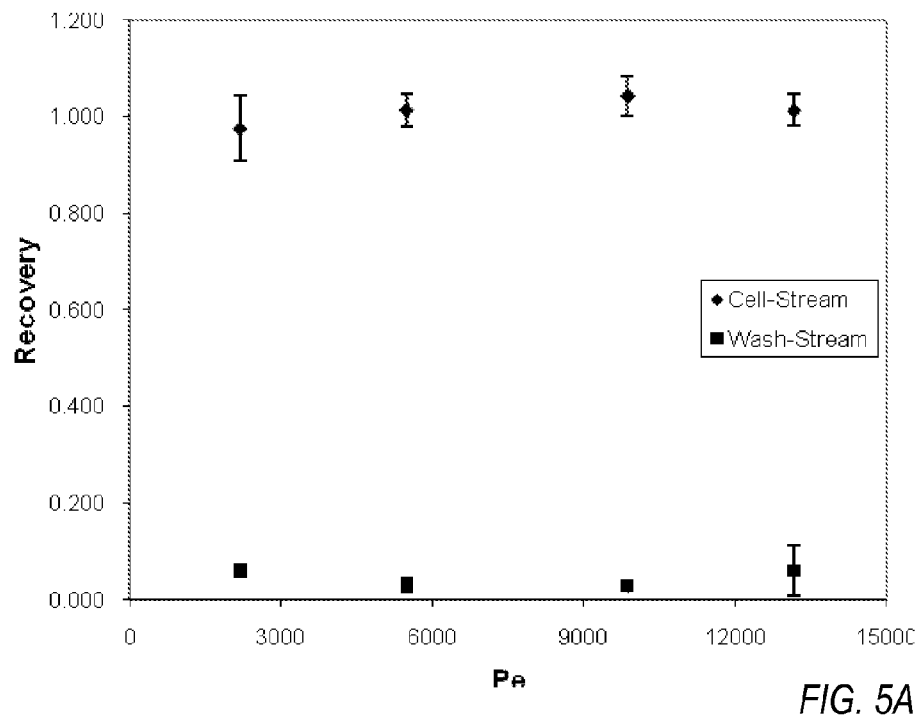
FIG. 5A includes plots of cell recovery from a device for cell volume factions ("CVF") of around 0.5%, at a flow rate of fq=0.019, according to an embodiment.
Figure 5B:
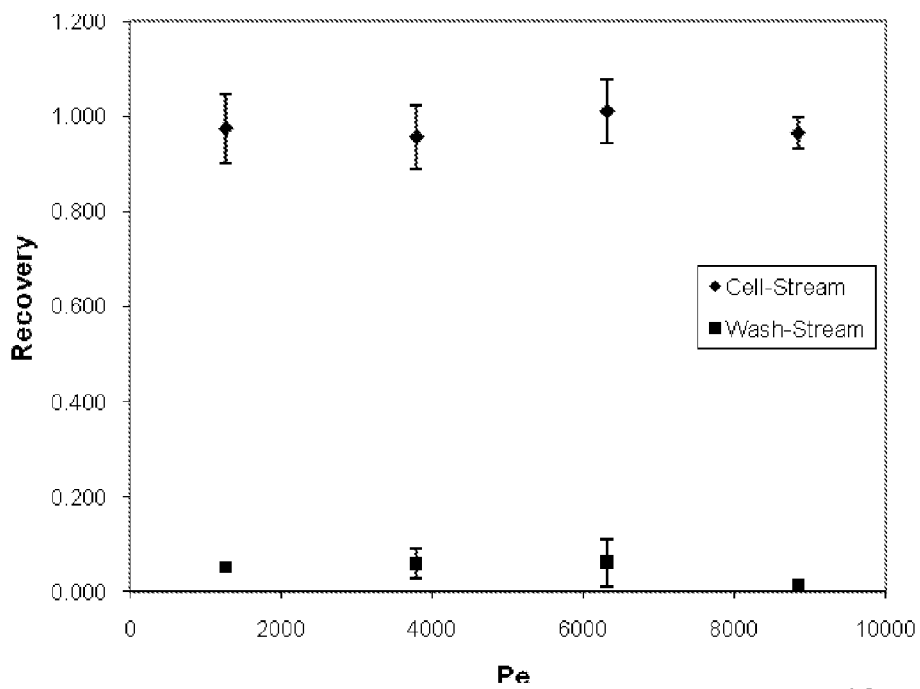
FIG. 5B includes plots of cell recovery from a device for CVF of around 0.5%, at a flow rate of fq=0.033, according to an embodiment.

Cell recovery from the device can be an important measure of device performance. Recovery can be assessed under a wide range of flow conditions. FIGS. 5A-B show cell recovery versus flow rate for $f_q$=0.19 and $f_q$=0.33, respectively. The figures show cell recovery from the device for CVF=0.5% (vol/vol) in a 10% DMSO+PBS solution. Cell stream flow rates can be varied between 0.5 and 3.5 ml/min Recovery accounts for the number of cells counted in the sample as well as cell viability. Samples can be taken at both the cell stream and wash stream outlets, and compared to samples from the device inlet, to account for cells lost to the removed wash solution. Each data point represents an average of at least 3 separate experiments, with error bars showing one standard deviation.

Figure 6:
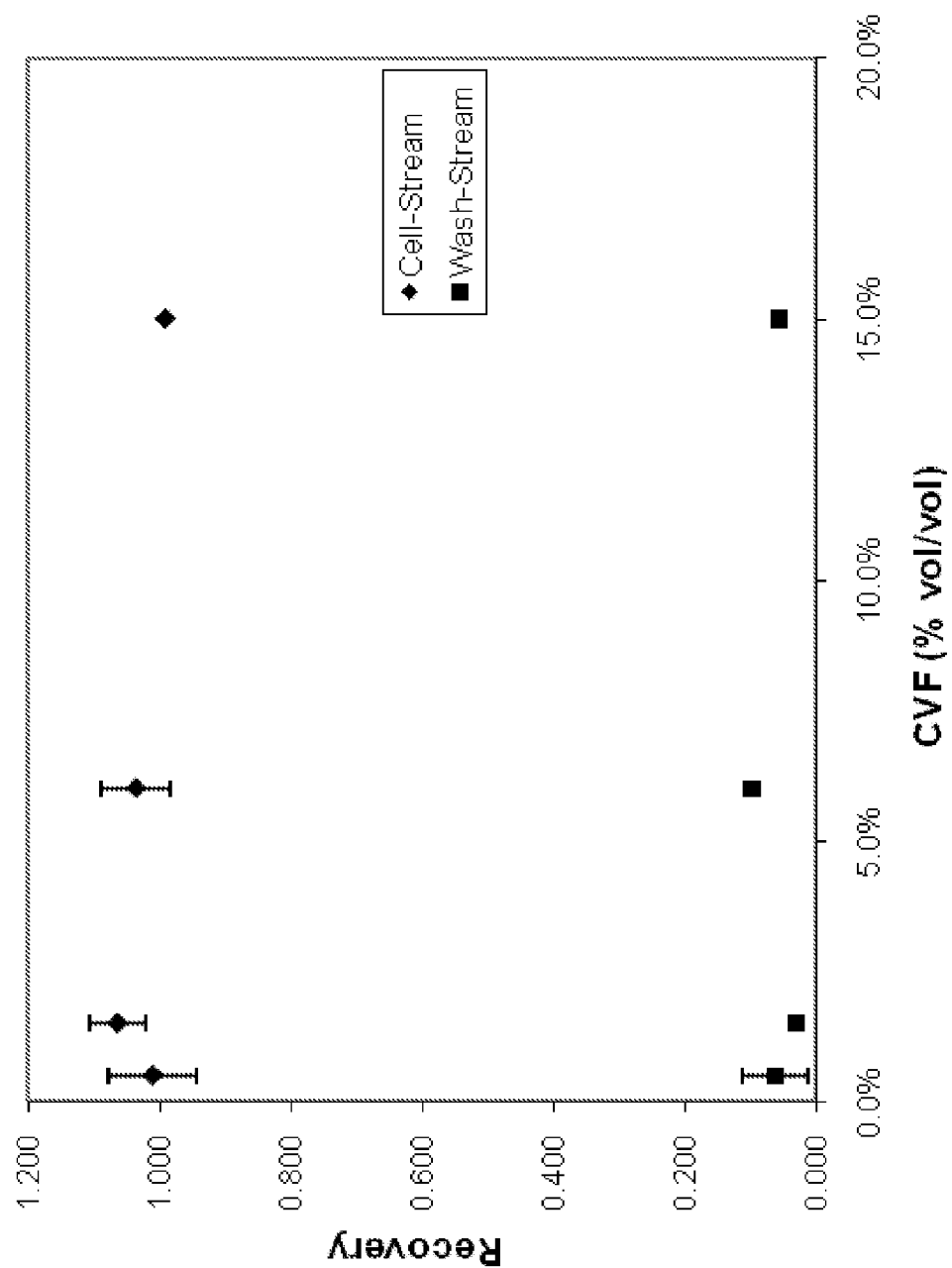
FIG. 6 includes plots of cell recovery from a cell stream outlet and a wash stream outlet versus CVF, according to an embodiment.

FIG. 6 shows the effect of cell volume fraction on cell recovery from the device. Processes can be performed with CVF=0.5, 1.5, 6, and 15%. The figure shows cell recovery from the cell stream outlet and wash stream outlets versus CVF. Processes can be performed using Qc=2.5 ml/min and fq=0.33. For CVF=0.5%, 1.5%, and 6%, processes can be performed in triplicate, with error bars showing one standard deviation. Results for CVF=15% represent a single experiment.

A cell stream flow rate of 2.5 ml/min (Pe=6313) and flow rate fraction of $f_q$=0.33 can be held constant for some or all of the embodiments in FIG. 6. Recovery can be measured at both the cell stream outlet and wash stream outlets. For CVF=0.5, 1.5, and 6%, data points represent the average of 3 separate trials, with error bars denoting one standard deviation. A single trial can be performed for CVF=15%.

Returning to FIGS. 3A-B, the plots show DMSO concentration at the outlet decreasing with increasing (1/Pe)*(L/d). At higher flow velocities (lower values of (1/Pe)*(L/d)), there can be less time for DMSO to diffuse from the sample stream to the wash stream before being separated again at the outlet, hence less DMSO can be removed at higher flow rates. Also, it can be noted that for each value of $f_q$, a "removal limit" can be approached for increasing values of (1/Pe)*(L/d). At lower flow velocities, the DMSO can continue to diffuse into the wash stream until the concentration gradient decreases or becomes negligible. It can also be noted in FIGS. 3A-B that for a given value of (1/Pe)*(L/d), DMSO removal can increase with decreasing $f_q$. This can be related to the relative volumes of the wash and sample streams. For lower $f_q$'s, there can be a proportionally larger volume of DMSO-free wash solution to accept DMSO diffusing from the sample stream. The flow-rate fraction can also affect the depth ratio, δ/d. Larger values of $f_q$ can represent that the sample stream occupies a larger width within the channel, δ, and hence the average distance a DMSO molecule travels in diffusion to the wash stream can be larger. The presence of a removal limit, combined with practical limitations on device design, can benefit from a multi-stage device that achieves a desired removal rate, such as a 95% removal of DMSO from the cell sample. Multiple stages of the microfluidic device can be linked in series, passing the sample from one to the next. Some embodiments include introducing fresh wash solution at each stage. FIG. 3A also shows that the numerical model can be in agreement with experimental results for predicting DMSO removal within the device. This behavior can be qualitatively similar to DMSO diffusion in a two-stream device.

FIG. 3B shows a comparison of DMSO removal in a vertical, three-stream device, to removal behavior in a two-stream, horizontal device. The three-stream arrangement increases diffusion from the cell stream to the wash stream, such as by doubling the interfacial area between the streams. Also, the average distance a DMSO molecule diffuses to leave the cell stream can be reduced. For a three-stream geometry, the normalized concentration can reach C*=0.50 at (1/Pe)*(L/d)=0.02, and approach the removal limit of C*=0.33 near (1/Pe)*(L/d)=0.10. For a two-stream device under similar conditions, C*=0.50 and the removal limit can be approached at (1/Pe)*(L/d)=0.08 and 0.40, respectively, which is approximately four times that for the three-stream device. Since the term (1/Pe)*(L/d) encompasses both length and velocity, this can be equivalent to showing that the three-stream device can remove the same amount of DMSO as the two-stream, but in either ¼ of the device length, or at four times the flow velocity. This can allow for either a smaller device size, faster processing rates, or a combination of the two factors.

In general, DMSO removal with cells follows trends similar to those without cells, with C* decreasing asymptotically with increasing (1/Pe)*(L/d). The presence of cells can reduce DMSO removal proportional to the volume of cells present within the sample, as DMSO can first leave the cells before it diffuses from the cell stream. For CVF=0.5%, the presence of cells causes an increase in C* at the device outlet of approximately 0.01, according to the model. For CVF=15%, the effect can be more notable, increasing C* by 0.06. For some flow rates, embodiments agree with the model. However, a deviation can be noted for the lowest flow rates tested, Qc=0.5 ml/min (Pe=1263). At very low flow rates, C* can be more than 0.10 higher than model predictions. In some examples, this is a result of density differences between the cell stream and wash streams. Both the cells and DMSO are denser than PBS, which causes the center stream to settle within the device and may result in the velocity profile deviating from parabolic. A non-parabolic velocity profile implies that the effective Pe for the specific experimental conditions can be higher than estimated and therefore the concentration of DMSO at the device outlet can be higher than expected. However, at higher flow rates (Qc=1.5 ml/min and higher), the effect becomes less noticeable. As overall flow velocities increase, residence time decrease, allowing less time for buoyancy forces to act. Also, settling velocity acquired by cells can be comparatively less significant as the overall flow velocity increases.

Laminar flow present in microfluidic devices can result in favorable motion of cells. As illustrated in FIGS. 4A and 4B, the images 402 and 406 confirm the cells are uniformly distributed through the x-z plane. Also, in both image 404 and 408 it can be seen that the cells are largely constrained to the central cell stream where shear forces are reduced or minimal and that cells do not migrate into the wash streams. Scale bars denote 115 μm, a width occupied by the cell stream assuming a parabolic velocity profile and for $f_q$=0.33. At the device inlet (e.g., 404), the cells are very concentrated in the center of the device, in a band around 60 μm wide, significantly narrower than 115 μm. Image 408 shows the device outlet. Again, cells largely remain in the center, though they can be more scattered than at the inlet, and a small portion of cells can be noted flowing outside of the predicted 115 μm cell stream. The distribution of the cells in a narrower region of the central stream can be consistent with the hypothesis described above that the velocity profile may not be parabolic across all three streams. Alternatively, if the cells are moving faster than the local fluid, slip velocity can result in hydrodynamic forces repelling cells from the channel walls and moving them towards the center.

Image sequences can be also used to track cells and approximate their velocities as they pass through the device. Though the accuracy of velocity estimates can be limited by camera frame rates, observation of ten cells traveling through the device center can show an average velocity of around 3.6 mm/s. This can be faster than the predicted 3.1 mm/s maximum flow velocity assuming a parabolic profile and neutral buoyancy of cells, and can represent that cells are more dense than the stream in which they are contained and thus settle in the vertically-oriented channel. Cells near the channel sides can be observed to move slightly slower, at around 3.0 mm/s, due to the presence of a boundary layer near the walls.

Cell recovery from the device can be a measure of device performance. Microfluidic devices have shown promise for cell processing due to reductions in stresses on cells compared to conventional methods. Contemporary approaches with two stream devices have shown that cell recovery from the device can be high under certain conditions. However, recovery can have a dependence on flow rates, potentially limiting the usable flow conditions for the device Similar restrictions on achievable flow rates with microfluidic devices are a common drawback. One of the benefits of the present subject matter is that embodiments can achieve higher recoveries for a wider range of flow conditions, particularly higher flow rates, to increase the clinical applicability of the device. Results in FIG. 5 show experiments for two different flow-rate fractions and CVF=0.5% over a wide range of flow rates. As can be seen, recovery can be high (greater than 95% for all flow conditions). At the same time, losses found in wash stream samples can be less than 6% for all cases. This shows that cell recovery from the device can be insensitive to flow rate, and does not restrict the usable flow conditions for diffusion or cell processing across the conditions tested.

Embodiments use various cell volume fractions to demonstrate limitations on the device's ability to handle a range of cell concentrations. Some microfluidic devices handle sparsely populated cell suspensions when compared to the 2% to 20% cytocrits used for cryopreservation. FIG. 6 shows recovery results with CVF from 0.5% to 15%. Losses to the wash stream can be low (<10%) for all conditions, while recovery can be greater than 95%. In some cases, total cells recovered (from both the cell and wash stream outlets) can exceed 100%, which can result from inaccuracies associated with cell enumeration using a hemacytometer.

High recoveries for a wide range of flow conditions can provide a marked improvement over contemporary devices, and particularly over centrifugation cell washing methods. In particular, the ability to handle high CVF samples is rare among contemporary microfluidic devices. Thus, the subject matter disclosed herein can help facilitate processing of clinically-relevant cell populations.

Microfluidic channels have been shown to be an effective option for removal of DMSO from cryopreserved cell suspensions. In various embodiments, changing the device design from a two-stream, horizontal arrangement to a three-stream, vertical device greatly improves device performance, both with respect to extraction of DMSO and recovery of cells from the sample. DMSO removal rate can be improved by a factor of four, allowing for either a more compact device or faster processing flow rates. Though a single device can be potentially capable of achieving the desired 95% removal of DMSO, embodiments using several channels in series can shorten processing times and reduce the required volume of wash solution. Cell recovery can be greater than 95% for certain flow rates and cell volume fractions. This can be an improvement of around 25% over centrifugation washing. Certain embodiments provide a device that can be capable of handling both cell-sparse (CVF=0.5%) and cell-dense (CVF=15%) samples at flow rates over 3 ml/min, a flexibility and speed uncommon in most microfluidic devices, thereby providing a viable alternative to centrifugation techniques for processing clinically relevant cell populations.

Figure 7:
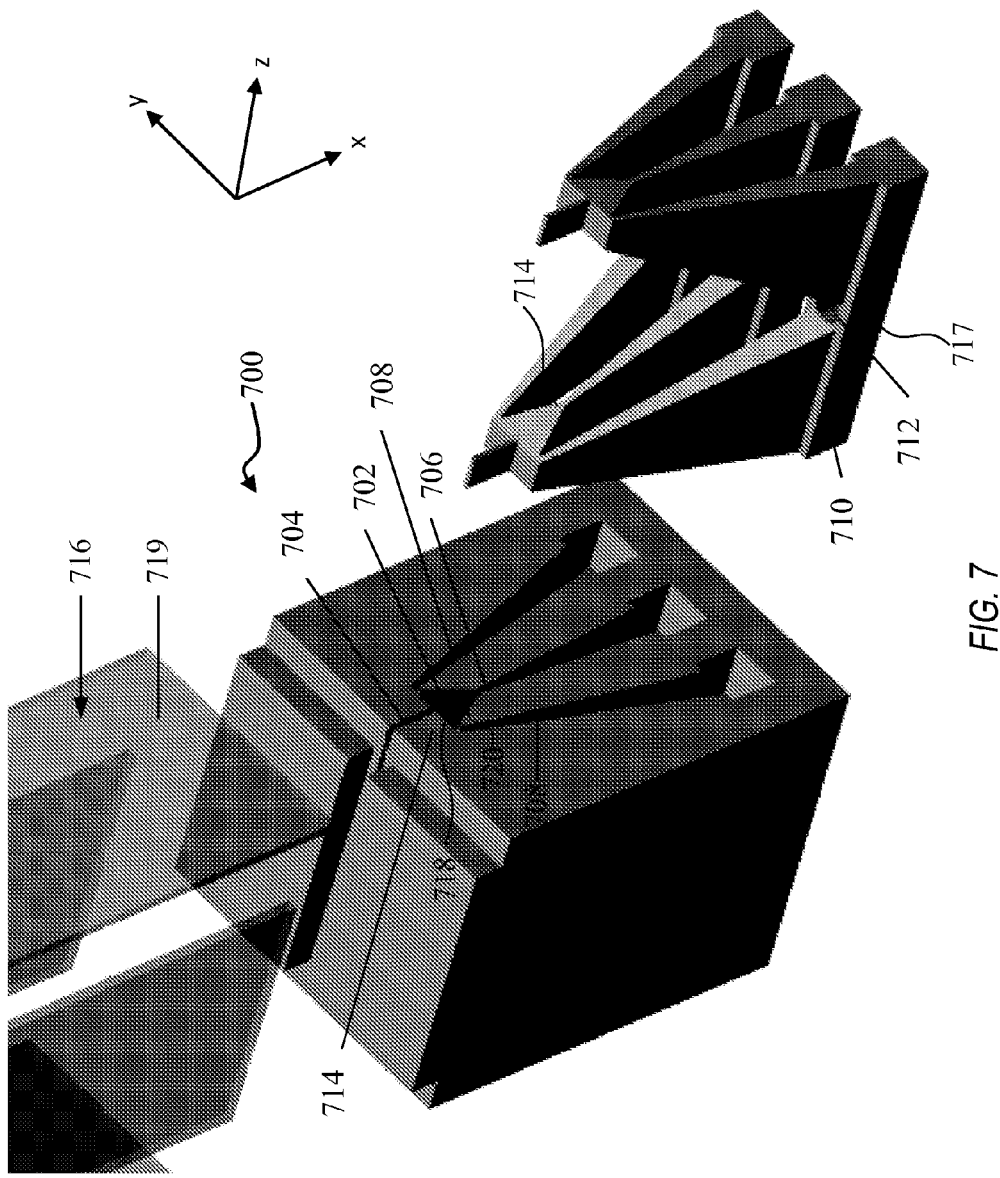
FIG. 7 is a perspective view of a cell separator, according to an embodiment.

FIG. 7 shows a perspective view of a portion of a microfluidic device 700 for cell separation, according to an embodiment. The illustrated devices, and their respective geometries, can be used at the inlet of devices described above (e.g., the inlet 208 in FIG. 2), such as to remove fluid from a cell stream and/or at an outlet (e.g., the outlet 212 in FIG. 2) of a device, such as to separate a cell stream from a wash stream. The device 700 can include a microchannel 716. FIG. 1 represents an example microchannel 102, with the cross-section illustrated in FIG. 1 being parallel to a front microchannel wall 719. In an example, the plenum 702 has a delta-shaped cross-section (along the x-y plane), with a vertex pointed vertically down in the x-direction, in alignment with gravity, but the present subject matter is not so limited. Leading into the plenum 702 is a microchannel 704, and leading from the plenum 702 is a cell collection channel 706. Wash fluid removal channels 708 extend laterally (e.g. long the y-axis) from the plenum 702, on opposite sides of the plenum. The channels terminate in respective outlets. A wash-channel outlet 712 is representative.

The figure shows an insert 710 that defines portions of the features 702-708. The insert 710 can define boundaries (along the z-axis) for channels 706 and 708. Channels 706 and 708 can remain nearly constant in cross-sectional area along their length extending away from the plenum 702. In other words, the channel at an outlet, such as after a central plenum 702, can be of a cross-sectional area perpendicular to flow (e.g., in the y-z plane for the cell sample collect channel 706) that remains substantially constant along the remainder of the channel, with the shape of the channel changing as the distance from the plenum outlet increases (e.g., in a direction corresponding to axis x for the cell sample collect channel 706). In an example, the channel shape is a high-aspect ratio rectangular shape at a top portion (in a direction corresponding to reduced x value), and a circular shape at a bottom portion of the wash-channel outlet 712, with a relatively constant cross sectional area between the portions. The circular shape can facilitate connection to a tube at the outlet. Cross-sectional area can vary within the central plenum 702, diminishing in arean in the x-direction.

Within the central plenum, it can be desirable to slow the fluid to allow time for gravity to pull the cells downward toward an outlet of the cell collection channel 706. To facilitate this, the geometry of the device 700 can be selected to control pressures and fluid velocity experienced at outlets of the plenum 702 where the plenum 702 meets a channel (e.g., 706 and/or 708).

In some embodiments, the device 700 is mounted vertically, so that a gravitational force can direct fluid from the microchannel 704 to the cell collection channel 706 (in the direction shown by axis x). In an example, flow through the plenum 702 can be laminar. Cells are heavier than fluid in the plenum 702, and thus, incoming cells are directed toward the cell collection channel 706, and wash fluid is directed toward the wash fluid removal channels 708.

The thickness (e.g., in the z-direction for the outlet opening to the cell sample collect channel 706) can be 500 micrometers. The depth of the plenum 702 along the x-axis, i.e., the distance from the microchannel 704 to the cell collection channel 706, can be substantially equal to a thickness along the y-axis. In some examples, this is about 25 millimeters. Such a proportion between the depth and the thickness can maintain mass flow rates to each outlet as constant. An average mammalian cell can be around 20 micrometers, and thus the inlet to the microchannel 704 can of a width in the y-direction around an order of magnitude greater than a cell diameter.

In certain examples, the plenum 702, along an x-y cross-section, has a first frustoconical shape with a center apex 714. Other possible shapes include a rounded bottom, such as a hemispherical cross-section, and a u-shape, in which a quarter-sphere extends from an outlet to the cell collection channel 706 to each of an outlet to a first wash fluid channel and an outlet to a second wash fluid channel. The plenum 702 can have a second frustoconical shape along an x-z plane, with a second center apex 717 of the second frustoconical shape disposed along an axis 90 degrees around the x-direction from a first center apex 714 of the first frustoconical shape.

Figure 9:
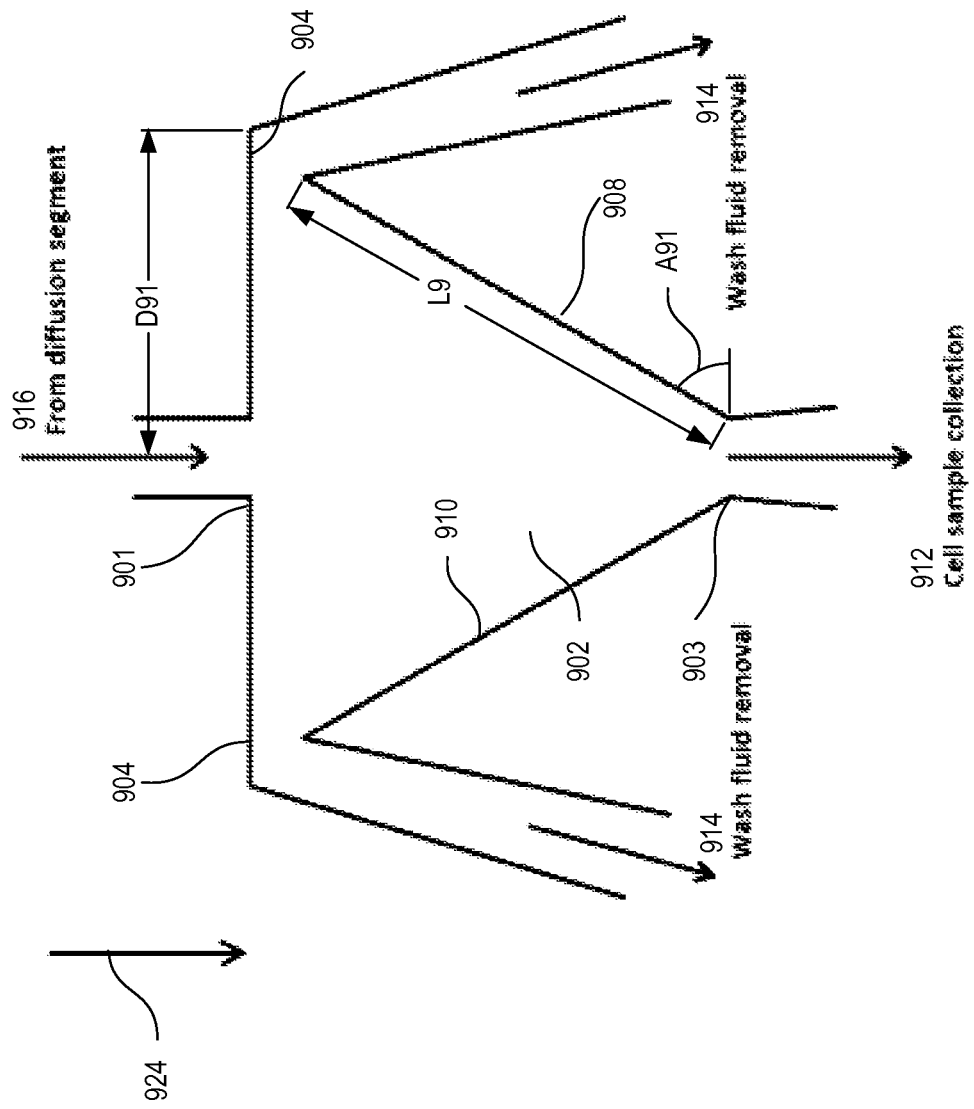
FIG. 9 shows a schematic depiction of a plenum and channels, according to an embodiment.

In an example, a distance (e.g., D91 in FIG. 9) between the inlet to the plenum and an outlet for removal of the excess or wash fluid can be selected based on the settling velocity of the cells. The distance can be specified to be far enough away so that cells would settle down instead of following stream lines out the outlet to the wash fluid channel. The dimension can be selected based on cell settling velocities. Cell inertia tends to carry each respective cell past the inlet to the plenum 702, and past flows extending to the wash channels 708. The lateral distance 718 (e.g., having a dimension D91 as shown in FIG. 9) can be selected to encourage cells to avoid the wash channels 708. In some examples, elevating or placing outlets to the wash channels 708 above the inlet to the plenum 702 from the microchannel 704 can also assist in discouraging cells from migrating to the wash streams 708. A length of each of the respective side-walls 720 (having a dimension L9 as shown in FIG. 9) as can also be selected to encourage cells to exit through the bottom outlet, such as due to a force such as gravity.

Figure 8:
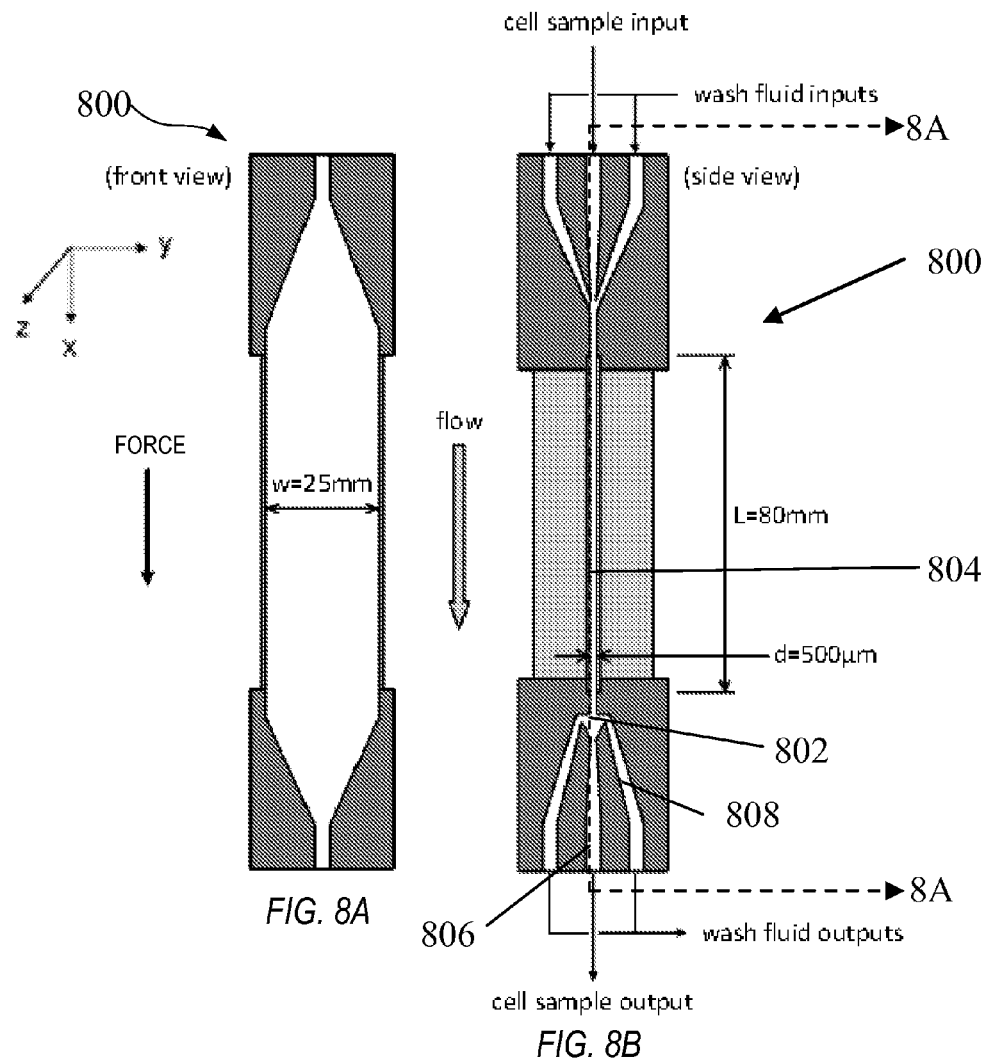
FIG. 8A is a front view of a cell separator, according to an embodiment.
FIG. 8B is cross-section side view of a cell separator, according to an embodiment.

FIG. 8A is a front view of a cell separator 800, according to an embodiment. FIG. 8B is cross-section side view of a cell separator, according to an embodiment. A delta-shaped plenum 802 is visible, as are channels extending toward the delta-shaped plenum. Leading into the plenum 802 is a microchannel 804, and leading from the plenum 802 is a cell collection channel 806. Wash fluid removal channels 808 extend laterally from the plenum 802, on opposite sides of the plenum 802. The illustration shows alignment with a force, such as gravity. It should be noted that the gravitational force can be a force caused by earth's gravitational field, or can be another force, such as a centrifugal force, sonic focusing, electrostatic or magnetic forces, and the like.

The illustration additionally shows exemplary dimensions. Other dimensions are possible without departing from the scope of the present subject matter. It should be noted that some embodiments do not include a second outlet to a wash fluid channel. The plane defined along line 8A-8A could comprise a surface sealed against the flow of fluid in the y and z directions. Such a configuration is compatible for sample collection from an inlet that includes two streams. For example, the device can be halved along line 8A-8A, and sealed along the cut, so that two streams are used, one including cell sample input and the other including a wash fluid input.

Figure 10:
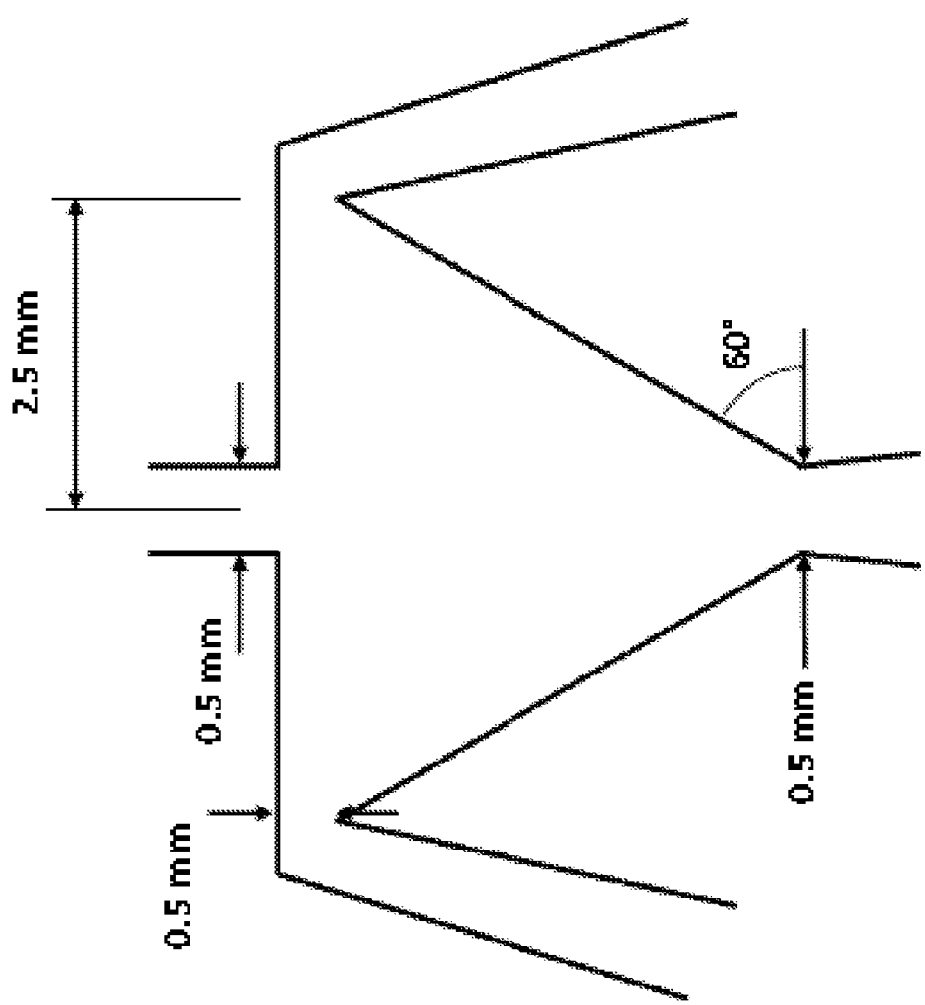
FIG. 10 shows dimensions of the plenum of FIG. 9, according to an embodiment.

FIG. 9 shows a schematic depiction of a plenum 902 and channels, according to an example. FIG. 10 shows exemplary dimensions of the plenum of FIG. 9. The geometry of plenum 902 is designed to encourage cells to reach, and even temporarily collect, at the sample collection point 903, while allowing the wash fluid to be removed and discarded with minimal loss of cells. This is because of one or more modes of operation influencing operation of the plenum 902.

A first mode of operation is associated with the 90 degree corner 901 proximal to which three fluid streams enter from the diffusion segment 916 (e.g., microchannel 704 in FIG. 7) the plenum 902. For sufficiently high flow velocities (e.g., flow velocities of a Stokes number of 10 or greater), the inertia of incoming cells can carry them past the corner 901 and into fluid streamlines moving toward the sample collection point 903 into cell collection 912, rather than following the wash fluid to the wash removal points 904 and ultimately wash fluid removal 914. The present subject matter is not limited to 90 degree corners, and other corners can be used. Additionally, it should be noted that a general shape of the plenum 902 is not limited to a delta-shape and can be of another shape that causes a pressure differential and control of fluid velocity and that leverages cell inertia to send cells toward a cell collection channel.

A second mode of operation can use a force 924, such as gravitational force, to direct cells toward the sample collection point 903. The cells in the sample are slightly more dense than the surrounding fluid, and as such, tend to settle downward. The cross-sectional area of the plenum can be larger than the microchannel to which it is attached. As such, the flow velocity can be significantly reduced in the plenum 902. There can be a horizontal distance D91 between 901 and 904, that can be selected to allow gravitational forces time to pull the cells downward toward the sample collection point 903, with an increased dimension resulting in additional downward motion of cells.

Alternatively, or in additional to this mode of operation, a distance L9, extending between 904 and 912, of a side-wall, such as side-wall 908 and/or side-wall 910, can be of a dimension selected to allow gravitational forces the time to pull the cells downward toward the sample collection point 903, with an increased dimension resulting in additional downward motion of cells. During such time, cells can settle into the sample collection channel. The angle A91 can also be of a dimension selected to allow gravitational forces the time to pull the cells downward toward the sample collection point 903, with an increased dimension resulting in additional downward motion of cells. A pressure differential between the sample collection point 903 and a diffusion segment 916 can be induced, but is not necessary.

The embodiments discussed herein provide additional benefits. One of the challenges to using a microfluidic device in a vertical orientation is that unless the device is perfectly vertical, it may not perform as desired. The design of the inlet and outlets discussed herein compensate for slight misalignment. The unique geometries are effective at flow rates significantly higher than contemporary microfluidic devices. Furthermore, recovery of cells from the device is high even for densely populated cell samples, such as those used in cell banking.

Figure 11:
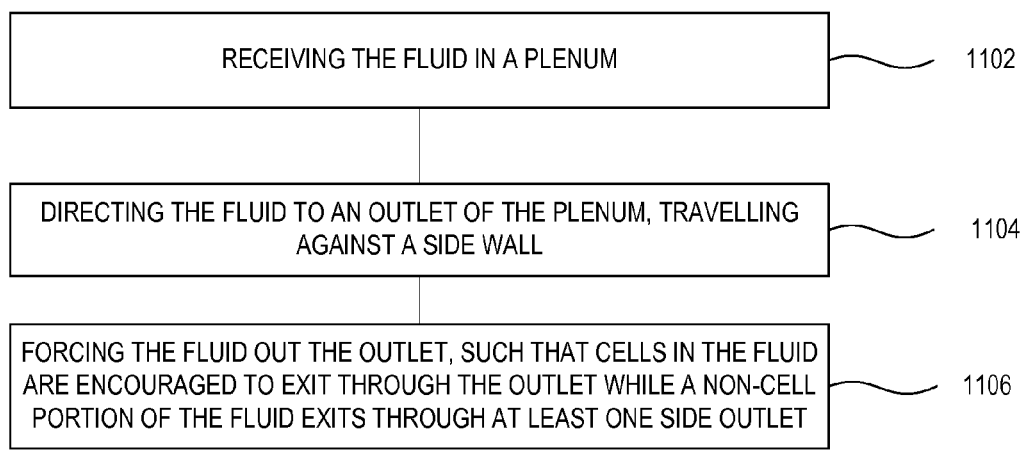
FIG. 11 shows a method of operating a device, according to an embodiment.

FIG. 11 shows a flow chart of a method of separating cells from a fluid under the influence of a force. At 1102, the method includes receiving the fluid through a centrally located top inlet of a plenum. At 1104, the method includes directing the fluid to a bottom outlet disposed below the top inlet, with the fluid directed against respective side-walls (e.g., 908, 910 in FIG. 9) extending between the bottom outlet and two or more side outlets to the side of the inlet and the bottom outlet, located above the bottom outlet. At 1106, the method includes forcing the fluid to travel a distance, between each of the two or more side outlets and the bottom outlet, such that cells in the fluid are drawn or encouraged to exit through the bottom outlet under the force while a non-cell portion of the fluid exits through the two or more side outlets above the bottom outlet.

A method can include selecting the distance from the inlet to one or more of the respective side outlets to draw or encourage cells to exit through the bottom outlet under the force. According to a method, forcing includes aligning the plenum with gravity. According to a method, forcing includes aligning the plenum on a centrifuge and forcing the fluid radially outward from the top inlet to the bottom outlet. According to a method, directing the fluid includes directing a cell-containing middle stream from the top inlet to the bottom outlet sandwiched in a laminar flow between two washing streams. A method can include washing a cryoprotective agent from the fluid.

Various Notes & Examples

Example 1 can include an apparatus for separating cells from a fluid under the influence of a force. The Example can include a plenum, defining a centrally located top inlet. The Example can include respective side outlets disposed on opposing sides of the top inlet. The Example can include a bottom outlet disposed below the top inlet, with the two or more side outlets disposed on opposite sides of the top inlet. In the Example, the plenum is configured to receive the fluid through the inlet, and direct it to the bottom outlet, against respective side-walls extending between the bottom outlet and the two or more side outlets. In the example, the distance between each of the two or more side outlets and the bottom outlet and/or the distance from the inlet to one or more of the at least two side outlets is selected to encourage cells to exit through the bottom outlet under the force.

Example 2 can include any of the preceding examples, wherein the respective side-walls are disposed at an angle to the force.

Example 3 can include any of the preceding examples, wherein the side-walls are disposed at a 60 degree angle to the force.

Example 4 can include any of the preceding examples, wherein the inlet opens to a sample collection channel that is wider along a z-direction than it is in a y-direction horizontally orthogonal to the z-direction, and wherein the force is directed in an x-direction that is orthogonal to both the z-direction and the y-direction.

Example 5 can include any of the preceding examples, wherein the respective side outlets are disposed below the inlet, to the side of the inlet along the y-direction.

Example 6 can include any of the preceding examples, wherein the plenum has a first frustoconical shape at a cross-section taken along an x-y plane and extruded along the z-direction.

Example 7 can include any of the preceding examples, wherein the plenum has a second frustoconical shape along an x-z plane extruded along the y-direction.

Example 8 can include any of the preceding examples, wherein a first outlet of the respective side outlets is disposed on a side of the x-z plane, and a second outlet of the respective side outlets is disposed on an opposite side of the x-z plane.

Example 9 can include any of the preceding examples, wherein each of the respective side outlets is elongated, extending along the z-direction.

Example 10 can include any of the preceding examples, wherein the bottom outlet is elongated, extending along the z-direction.

Example 11 can include any of the preceding examples, wherein each of the respective side outlets and the bottom outlet is substantially of the same area.

Example 12 can include any of the preceding examples, wherein a top-wall defining the plenum extends along the y-z plane. The Example can include the inlet opening disposed through the top-wall, and a top side of each of the respective side outlets is disposed abutting the top-wall.

Example 13 can include any of the preceding examples, wherein the plenum is defined by the top-wall and the respective side-walls.

Example 14 can include a method of separating cells from a fluid sample under the influence of a force. The Example can include receiving the fluid through a centrally located top inlet of a plenum. The Example can include directing the fluid to a bottom outlet disposed below the top inlet, with the fluid directed against respective side-walls extending between the bottom outlet and two or more side outlets to the side of the inlet and the bottom outlet, located above the bottom outlet. The Example can include forcing the fluid to travel a distance, between each of the two or more side outlets and the bottom outlet, such that cells in the fluid are encouraged to exit through the bottom outlet under the force while a non-cell portion of the fluid exits through the two or more side outlets above the bottom outlet.

Example 15 can include any of the preceding examples, comprising selecting the distance from the inlet to one or more of the respective side outlets to encourage cells to exit through the bottom outlet under the force.

Example 16 can include any of the preceding examples, wherein forcing includes aligning the plenum with gravity.

Example 17 can include any of the preceding examples, wherein forcing includes aligning the plenum on a centrifuge and forcing the fluid radially outward from the top inlet to the bottom outlet.

Example 18 can include any of the preceding examples, wherein directing the fluid includes directing a cell-containing middle stream from the top inlet to the bottom outlet sandwiched in a laminar flow between two washing streams.

Example 19 can include any of the preceding examples, comprising washing a cryoprotective agent from the fluid.

Example 20 can include a system comprising a fluid plenum chamber having an inlet port, a first outlet port, and a second outlet port, with the chamber configured to modulate fluid flow between the inlet port and the first outlet port and to modulate fluid flow between the inlet port and the second outlet port, the chamber having a wall configuration such that a first constituent of a fluid at the inlet port is directed to the first outlet port and a second constituent of the fluid is directed to the second outlet port when the fluid is subjected to a force aligned with an axis between the inlet port and the first outlet port.

Example 21 can include any of the preceding examples, wherein the second outlet port is one of a pair of outlet ports disposed on opposite sides of the inlet port.

Example 22 can include any of the preceding examples, comprising a syringe pump to pump a cell-laden fluid and a pair of wash streams into the inlet port, with the pair of wash streams sandwiching the cell-laden fluid therebetween.

Example 23 can include any of the preceding examples, wherein the syringe pump is to pump the wash streams out of the second outlet port.

Example 24 can include any of the preceding examples, wherein the size of the first outlet port is sized to temporarily collect cells of the cell-laden fluid, thereby creating a pressure differential to encourage wash of the wash streams through the pair of outlet ports.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of separating cells from a fluid sample under the influence of a force, comprising:

receiving a fluid through a centrally located top inlet of a plenum, the plenum having a diminishing volume in a direction of the force with a first cross-sectional area proximate the inlet larger than a second cross-sectional area proximate a bottom outlet of the plenum;

directing the fluid toward the bottom outlet disposed below the top inlet, the fluid directed against respective side-walls of the plenum, the side walls each extending at an acute angle with respect to the direction of the force and positioned to the side of the inlet and the bottom outlet; and flowing the fluid in the plenum under the force, the plenum having a distance between each of two or more side outlets and the bottom outlet, the distance selected such that cells in the fluid exit through the bottom outlet under the force while a non-cell portion of the fluid exits through the two or more side outlets above the bottom outlet.

2. The method of claim 1, comprising selecting a second distance from the inlet to one or more of the two or more side outlets to encourage cells to exit through the bottom outlet under the force.

3. The method of claim 1, wherein flowing the fluid includes aligning the plenum with gravitational force to pull the cells downward from the top inlet to the bottom outlet.

4. The method of claim 1, wherein flowing the fluid includes aligning the plenum on a centrifuge and applying a centrifugal force to the fluid to pull the cells radially outward from the top inlet to the bottom outlet.

5. The method of claim 1, wherein directing the fluid includes directing a cell-containing middle stream from the top inlet to the bottom outlet sandwiched in a laminar flow between two washing streams.

6. The method of claim 1, comprising washing a cryoprotective agent from the fluid.

7. The method of claim 1, wherein the acute angle comprises a 60 degree angle to the force.

8. The method of claim 1, wherein the force is aligned substantially parallel with an axis extending between the top inlet and the bottom outlet.

9. A method of separating cells from a fluid sample under the influence of a force, comprising:

moving a fluid through a plenum, the plenum having a diminishing volume in a direction of the force with a first cross-sectional area proximate an inlet of the plenum larger than a second cross-sectional area proximate a first outlet of the plenum, the plenum having an end wall and at least two side walls, the fluid entering the plenum at the inlet on the end wall and exiting the plenum at the first outlet corresponding to a vertex of the two side walls, and the force is aligned substantially parallel with a line between the inlet and the first outlet;

directing a portion of the fluid against the side walls of the plenum with a non-cell portion of the fluid exiting the plenum through two or more secondary outlets, the two or more secondary outlets disposed between the end wall and the side walls; and wherein the sidewalls have a first dimension between each of the two or more secondary outlets and the first outlet, and the plenum has a second dimension between the inlet and each of the two or more secondary outlets, the first dimension and the second dimension selected such that a cell in the fluid exits through the first outlet under the force.

10. The method of claim 9, comprising selecting one of the first distance and the second distance based on a settling velocity of the cells in the fluid.

11. The method of claim 9, wherein the second distance extends laterally in a direction orthogonal to the force.

12. The method of claim 9, wherein the force comprises gravitational force and the vertex is in alignment with the gravitational force to pull the cells downward from the inlet to the first outlet.

13. The method of claim 9, wherein the force comprises centrifugal force and the vertex is in alignment with the centrifugal force to pull the cells radially outward from the inlet to the first outlet.

14. The method of claim 9, wherein directing the portion of the fluid includes directing a cell-containing middle stream from the inlet to the first outlet sandwiched in a laminar flow between two washing streams.

15. The method of claim 9, comprising washing a cryoprotective agent from the fluid.

16. The method of claim 9, wherein each of the side-walls are disposed at acute angles to the force.

17. The method of claim 9, wherein the plenum has a delta shaped cross-section when viewed normal to a plane.

18. A method of separating cells from a fluid sample under the influence of gravitational force, comprising:

orienting a plenum vertically, the plenum having a diminishing volume in a direction of the gravitational force with a first cross-sectional area proximate a centrally located top inlet relatively larger than a second cross-sectional area proximate a bottom outlet;

receiving a fluid through the top inlet of the plenum;

directing the fluid toward the bottom outlet disposed below the top inlet, the fluid directed against respective side-walls extending between the bottom outlet and two or more side outlets to the side of the inlet and the bottom outlet, located above the bottom outlet; and flowing the fluid within the plenum under the gravitational force, the plenum configured to control pressures and fluid velocity experienced at the bottom outlet and the two or more side outlets such that cells in the fluid exit through the bottom outlet under the gravitational force while a non-cell portion of the fluid exits through the two or more side outlets above the bottom outlet.

19. The method of claim 18, wherein orienting the plenum vertically includes disposing the respective side-walls at acute angles to the gravitational force.

20. The method of claim 18, wherein orienting the plenum vertically aligns the force substantially parallel with an axis extending between the top inlet and the bottom outlet.

21. The method of claim 18, providing the plenum with a first distance between at least one of the two or more side outlets and the bottom outlet, and a second distance from the inlet to one or more of the two or more side outlets, the first distance and the second distance selected such that the cells in the fluid exit through the bottom outlet.

22. The method of claim 21, wherein the second distance extends laterally in a direction orthogonal to the gravitational force.

23. The method of claim 18, wherein directing the fluid includes directing a cell containing middle stream from the top inlet to the bottom outlet sandwiched in a laminar flow between two washing streams.

24. The method of claim 18, comprising washing a cryoprotective agent from the fluid.

* * * * *

UNITED STATES PATENT AND TRADEMARK OFFICE
CERTIFICATE OF CORRECTION

PATENT NO. : 9,556,412 B2  
APPLICATION NO. : 14/394693  
DATED : January 31, 2017  
INVENTOR(S) : Hubel et al.

Page 1 of 2

It is certified that error appears in the above-identified patent and that said Letters Patent is hereby corrected as shown below:

In the Drawings

On Sheet 3 of 11, Fig. 3A, Line 1, delete "fq=0.15" and insert --$f_q$=0.15-- therefor On sheet 3 of 11, Fig. 3A, Line 2, delete "fq=0.15" and insert --$f_q$=0.15-- therefor On sheet 3 of 11, Fig. 3A, Line 3, delete "fq=0.19" and insert --$f_q$=0.19-- therefor On sheet 3 of 11, Fig. 3A, Line 4, delete "fq=0.19" and insert --$f_q$=0.19-- therefor On sheet 3 of 11, Fig. 3A, Line 5, delete "fq=0.33" and insert --$f_q$=0.33-- therefor On sheet 3 of 11, Fig. 3A, Line 6, delete "fq=0.33" and insert --$f_q$=0.33-- therefor In the Specification In Column 2, Line 25, delete "fq=0.019," and insert --$f_q$=0.19,-- therefor In Column 2, Line 27, delete "fq=0.033," and insert --$f_q$=0.33,-- therefor In Column 5, Line 16-18, delete " $\frac{V_i}{V_i}$ " and insert -- $\frac{V_i}{V_i}$ -- therefor In Column 6, Line 44, delete "ml/min)" and insert --ml/min).-- therefor In Column 7, Line 12, delete "spectrophotometry" and insert --spectrophotometry.-- therefor In Column 8, Line 14, delete "(fq)." and insert --($f_q$).-- therefor Signed and Sealed this  
Fifteenth Day of May, 2018

Andrei Iancu  
*Director of the United States Patent and Trademark Office*

CERTIFICATE OF CORRECTION (continued)
U.S. Pat. No. 9,556,412 B2

In Column 8, Line 35, delete "fq=0.33." and insert --$f_q$=0.33.-- therefor

In Column 9, Line 28, delete "ml/min" and insert --ml/min.-- therefor

In Column 9, Line 40, delete "Qc=2.5" and insert --$Q_c$=2.5-- therefor

In Column 9, Line 41, delete "fq=0.33." and insert --$f_q$=0.33.-- therefor

In Column 10, Line 49, delete "Qc=0.5" and insert --$Q_c$=0.5-- therefor

In Column 10, Line 60, delete "(Qc=1.5" and insert --($Q_c$=1.5-- therefor

In Column 11, Line 40, delete "device" and insert --device.-- therefor